(12) United States Patent
Lundborg

(10) Patent No.: US 8,530,424 B2
(45) Date of Patent: Sep. 10, 2013

(54) SYSTEM AND METHOD TO IMPROVE SENSORY FUNCTION

(75) Inventor: Göran Lundborg, Genarp (SE)

(73) Assignee: Ossur HF, Reykjavik (IS)

( * ) Notice: Subject to any disclaimer, the term of this patent is extended or adjusted under 35 U.S.C. 154(b) by 339 days.

(21) Appl. No.: 12/678,982

(22) PCT Filed: Sep. 11, 2008

(86) PCT No.: PCT/SE2008/000507
§ 371 (c)(1),
(2), (4) Date: Mar. 18, 2010

(87) PCT Pub. No.: WO2009/038514
PCT Pub. Date: Mar. 26, 2009

(65) Prior Publication Data
US 2010/0196449 A1    Aug. 5, 2010

(30) Foreign Application Priority Data
Sep. 18, 2007   (SE) .................... 0702071-2

(51) Int. Cl.
  *A61K 38/00*     (2006.01)
  *A61F 13/00*     (2006.01)
(52) U.S. Cl.
  USPC ......................... 514/18.2; 424/449
(58) Field of Classification Search
  USPC ....................... 514/18.2; 424/449
  See application file for complete search history.

(56) References Cited

U.S. PATENT DOCUMENTS

2004/0101582 A1* 5/2004 Wolicki ................ 424/760
2005/0112183 A1   5/2005 Galer

OTHER PUBLICATIONS

Lidocaine, Retrieved online [Mar. 17, 2012], Retrieved from URL:<http://www.medicinenet.com/lidocaine-oral_ointment/article.htm>.*
Rosén, B., et al., "Improved Sensory Relearning After Nerve Repair Induced by Selective Temporary Anaesthesia—A New Concept in Hand Rehabilitation," Journal of Hand Surgery 31(2):126-132, Apr. 2006.
International Search Report mailed Nov. 28, 2008, issued in corresponding PCT/SE2008/000507, filed Sep. 11, 2008.

* cited by examiner

*Primary Examiner* — Lezah W Roberts
*Assistant Examiner* — Nanette Holloman
(74) *Attorney, Agent, or Firm* — Workman Nydegger

(57) ABSTRACT

A system and method to improve sensory functions in the hand or foot by dermal topical application of a local anaesthetic substance to adjacent skin areas, using a tailored application device or kit specially designed to fit the size and anatomical shape of the body part which is to be anesthetized. The concept is to block sensory input from the anesthetized skin area hereby inducing a functional reorganization in sensory brain cortex resulting in enhanced sensory functions in body parts adjacent to the anesthetized area with focus on the hand and sole of the foot.

15 Claims, No Drawings

SYSTEM AND METHOD TO IMPROVE SENSORY FUNCTION

FIELD OF INVENTION

The present invention relates to a system for anaesthesia of a defined skin area in extremities using a tailored application device specially designed to fit the size and anatomical shape of the body part to be anaesthetised. Anaesthesia of a body part results in a "silent" area in brain cortex, corresponding to the cortical projection of the anaesthetised body part. This allows a rapid expansion of adjacent cortical projectional areas corresponding to neighbouring body parts, hereby allowing improved sensory functions in said neighbouring body parts.

BACKGROUND OF THE INVENTION

Hand Sensation

The sensory function of the human hand area is unique and essential for hand function. Protective sensibility is of fundamental importance since it protects the hand from be injured by mechanical, thermal or chemical stimuli. Functional sensibility, or tactile gnosis, helps to, without vision, define the structure of textures and to understand the shape of small items (Katz, 1989; Klatsky, et al., 1987). The sense of touch is essential for making a hand "belonging to the body". A hand without sensory function is perceived as a foreign body and may even be denied by the owner (Ramachandran, 1998). In addition, regulation of grip force and execution of delicate motor task in the hand are dependent on sensory input from the hand to the central nervous system.

The sensibility of the glabrous skin of the hand is based on four types of mechanoreceptors, localised in subepidermal and subcutaneous areas, responding to static pressure of vibrotactile stimuli (Johansson, Birznieks, 2004; Johansson, Vallbo, 1979). Among receptors responding to vibration are Meissner's corpuscles, located in the subepidermal papillae, with small receptive fields (fast adapting type I-FAI receptor) and Pacini's corpuscles, located in subcutaneous layers possessing large receptive fields (fast adapting type II-FAII receptor). The Merkel cells, located just beneath epithelium, respond to static pressure and have small receptive fields (slowly adapting-type I-SAI receptor). Ruffini's organ, located subcutaneously, responds mainly to stretching (SAII receptors).

The Cortical Body Map

The various parts of the body are represented in projectional areas in the sensory and motor cortex of the brain, constituting a cortical body map (Kaas, 1997; Merzenich, Jenkins, 1993). In somatosensory cortex the projectional area of the various body parts are in proportions to their sensory functions: body parts with exceptionally well developed sensation like the hand or face occupy a major part of sensory brain cortex.

Electrical signals, elicited by touching the hand are transferred via nervous pathways primarily to contralateral sensory brain cortex, here constituting a neural map of the hand, also called the cortical hand map. In primates, exact hand- and finger representations have been meticulously outlined by direct recording from the cortical surface (Kaas, 1997; Merzenich, Jenkins, 1993; Merzenich, et al., 1978; Merzenich, et al., 1987), and in humans a corresponding cortical mapping of the hand has been identified by use of various brain imaging techniques such as magneto-encephalography (MEG) and functional magnetic resonance imaging (fMRI) (Hari, et al., 1993; Naas, 1997; Maldjian, et al., 1999; van Westen, et al., 2004). In the cortical hand map the individual fingers are well separated by sharp boarders, the thumb being located inferiorly in relation to the fifth finger. The forearm projectional area is located immediately superior to the little finger.

Brain Plasticity and Cortical Competition

It was long believed that the cortical body map was firmly established in the adult brain, that the brain was "hard-wired" from the start and that sensory body representations in the mature brain was fixed and not capable of functional reorganisations. However, according to evolving concepts over the past decades, the brain is much more plastic than was previously believed possessing a very substantial capacity for cortical functional reorganisations even at the adult stage (Bach-y-Rita, 1967; Bach-v-Rita, 1981; Bach-y-Rita, 1990; Bach-y-Rita, 1994; Buonomano, Merzenich, 1998). In adult primates there is a capacity for rapid cortical reorganisations in the sensory cortex (Merzenich, et al., 1978; Merzenich, et al., 1983; Merzenich, et al., 1987; Merzenich, et al., 1984). The cortical projection of the hand is experience-dependent and depending on factors like activity and extent of sensory inflow. For instance, amputation of an arm results in total arrest of all sensory inflow from the arm to the brain—a so called de-afferentiation. In such cases there is a rapid displacement of the adjacent face area towards the hand representation in sensory cortex (Elbert, et al., 1994), which may give rise to a strange clinical phenomenon already 24 hours after an arm amputation: the missing hand can be mapped in the face so that touch of specific areas of the face can give rise to tactile sensations in individual fingers of the missing hand (Borsook, et al., 1998; Flor, et al., 1998; Flor, et al., 1995; Ramachandran, et al., 1992).

Central Nervous Effects of Cutaneous Anaesthesia Fast functional changes in cortical representation may be induced also as a result of anaesthetic blocks. Finger anaesthesia of healthy voluntaries results, within minutes, in a cortical expansion of the adjacent fingers which hereby occupy areas that cover the former projection site of the anaesthetised finger (Rossini, et al., 1994). Cutaneous anaesthesia of the forearm, using prilocaine/lidocaine (EMLA) results in rapid improvement of sensory functions in the hand, presumely due to expansion of the cortical hand sensory projection giving the hand access to more brain space (Bjorkman, et al., 2004), and in nerve injured patients repeated application of prilocaine/lidocaine to the forearm results in enhanced sensory recovery of the hand (Rosen, et al., 2006). Preliminary studies indicate that the principle is valid also for the lower extremity: application of prilocaine/lidocaine to the calf of the lower limb results in improved sensation in the sole of the foot in healthy voluntaries.

Example 1. A 62 year old female dental technician, working with vibrating tools for 15 years, suffer from neuropathy with impaired sensibility of the hand. She experienced numbness and impaired fine discriminative sensibility of the hand. 40 g of EMLA crème was applied to the volar aspect of the forearm within a 5×15 cm cutaneous area. The crème was covered with a thin plastic membrane, in turn covered with a piece of textile (a thin towel) designed to fit the size and shape of the forearm, wrapped around the forearm and fixated to itself by tape. The wrapping was applied for one hour. Before and one hour after application of EMLA crème two-point discrimination, perception to touch and vibration thresholds were assessed in the long finger. After EMLA application two-point discrimination improved from 4 to 2.2 mm, and capacity to feel touch improved from 0.5 g to 0.04 g. Repeated treatment sessions for two mounts resulted in persistent improvement, and in a VAS-scale (1=worst possible, 10=best possible) the score improved from 2 to 8.

Example 2. In a healthy 26 year old volunteer the sensibility of the sole of the foot was assessed with focus on vibration sense volar to the first metatarsal head. 40 g EMLA crème was applied to the calf over a skin area distal to the knee measuring 10-15 cm. In analogy with example 1 the EMLA crème was covered with a thin plastic membrane, in turn covered with a piece of textile, designed in shape after the size and shape of the calf, wrapped around the lower leg below the knee and fixated to itself by tapes. EMLA crème was applied for one hour and then removed. The treatment resulted in significantly improved vibration sense with thresholds for vibration perception decreasing from 130 to 120 dB whitn 250 Hz, and from 115 to 105 dB within 15 Hz.

SUMMARY OF THE INVENTION

A system and method for topical application of a local anaesthetic substance to a defined body part in the upper or lower extremity by a tailored specially designed application device is proposed in order to improve sensory functions in the body part close to the anaesthetised area. The concept is based on current insight into brain plasticity mechanism, indicating that anaesthesia of a body part and corresponding de-afferentiation of the corresponding cortical projection in sensory cortex allows expansion of the adjacent projection areas of adjacent body parts. Such a cortical reorganisation may occur within minutes or hours after application of the anaesthetic substance, but is reversible when the anaesthetic effect is running out. To enhance and prolong the effects of such treatment an anaesthetic substance with long-term effects can be used, either existing anaesthetic substances with known long-term effect like Bupivakaine (marcain), Levobupivacaine (Foster, Markham, 2000), Rupivakaine (Narop) or any other anaesthetic substance with analogous effects. The molecular composition of the drug delivery system may be such as to facilitate penetration through the skin to induce anaesthetic effects on superficial as well as deep neural structures in the anaesthetised skin area. An example of a suitable lipid drug delivery system is the use of liquid crystalin faces (cubic and hexagonal), for instance Elyzol, where the active substance is disbursed in a lipid matrix to be delivered into tooth pockets.

Some anaesthetic agens, for instance Prilocaine/lidocaine (EMLA) is today available in small patches to be applied, mainly in children, on skin areas where an intravenous injection is planned. According to the present invention the anaesthetic substance should however be incorporated in and delivered by a plaster, stocking, patch, sleeve, socket or any other type of cover or analogous equipment, tailored and specifically designed in size and anatomical shape to be easily applied to a defined body part in the upper or lower extremity. In the arm, the design of the equipment should be such to cover the volar and/or dorsal area of the forearm or any suitable area in the arm or hand. It should be easily applied and easily removed, for instance through fastening of the cover, wrapped around the forearm or lower limb, by Velcro-fastening or analogous fastening mechanism or a zipper mechanism. The drug delivery system containing the anaesthetic agent can be incorporated in a stocking, which is rolled or put onto the forearm in a centripetal direction. In such cases the hand may be temporarily covered by a glove to protect it from the anaesthetic agent when the stocking is rolled or pulled onto the forearm. In such cases, after application of a stocking, the glove is removed. The stocking applied on the forearm provides a protective layer for the anaesthetised skin. The stocking, plaster, patch, sleeve or socket containing the drug delivery system, can be removed after a define time period, for instance 1-4 hours. To give further protection to the skin of the forearm a new clean stocking or protective device can now be applied to provide protection for the anaesthetised forearm.

In the lower extremity an analogous procedure may be carried out. As a first step a stocking is applied to the foot distal to the ankle to provide protection from the anaesthetic agent. Then a stocking, containing the anaesthetic drug delivery system can be rolled upon the crus or pulled along the outside of the crus. At this time the stocking, applied to the foot, can be removed. The stocking, applied distal to the knee, now protects the anaesthetised skin area from injury but can be removed after a defined time period, for instance 1-4 hours. Since the anaesthetic effect may last for a longer time another stocking, covering the lower limb from ankle level to knee level could be applied to give further protection. In the lower limb the substance can also be applied by a plaster, patch, sleeve, socket or any device or analogous device, covering appropriate parts of the calf region or/and the anterior aspect of the limb or/and the dorsal part of the foot. The cover, containing the anaesthetic agent, can be wrapped around the limb and fixated in place by use of Velcro-fastening or analogous fastening mechanism or a zipper. A suitable specially designed tailored stocking, plaster, patch, sleeve or analogous device can be constructed and applied to any other parts of the body when a treatment effect, according to what is said above, is desired. In the arm the application of the anaesthetic substance represents a treatment to improve sensation in hands with impaired sensation, such as after injury to the peripheral or central nervous system, nerve compression lesions such as carpal tunnel syndrome as well as neuropathies based on vibration exposure or diabetes or any other type of neuropathy. In the lower limb the main indication for application of the anaesthetic agents is neuropathy of the foot, for instance in diabetes neuropathy, with impaired sensibility of the foot sole and risk for skin damage and ulcer formation. Such impaired sensibility may be associated with impaired balance as well. Thus, cutaneous anaesthesia of the lower part of the limb (crus) can be used also to improve balance.

REFERENCES

Bach-y-Rita P (1967). Sensory plasticity. Applications to a vision subsittution system. Acta Neurol Scand 43: 417-426.

Bach-y-Rita P (1981). Brain plasticity as a basis of the development of rehabilitation procedures for hemiplegia. Scand J Rehab Med 13: 73-83.

Bach-y-Rita P (1990). Brain plasticity as a basis for recovery of function in humans. Neuropsychologia 28: 547-554.

Bach-y-Rita P (1994). The brain beyond the synapse: a review. Neuroreport 5: 1553-1557.

Bjorkman A, Rosen B, Lundborg G (2004). Acute improvement of hand sensibility after selective ipsilateral cutaneous forearm anaesthesia. Eur J Neurosci 20: 2733-2736.

Borsook D, Becerra L, Fishman S, Edwards A, Jennings C, Stojanovic M, Papinicolas L, Ramachandran V, Gonzalez R, Breiter H (1998). Acute plasticity in the human somatosensory cortex following amputation. Neuro Report 9: 1013-1017.

Buonomano D, Merzenich M (1998). Cortical plasticity: from synapses to maps. Arrau Rev Neurosci 21: 149-186.

Elbert T, Flor H, Birbaumer N, Knecht S, Hampson S, Larbig W, Taub E (1994). Extensive reorganization of the somatosensory cortex in adult humans after nervous system injury. Neororeport 5: 2593-2597.
Flor H, Elbert T, Muhlnickel W, Pantev C, Wienbruch C, Taaub E (1998). Cortical reorganization and phantom phenomena in congenital and traumatic upper-extremity amputees. Exp Brain Res 119: 205-212.
Flor H, Elbert T, Wienbruch C, Pantev C, Birbaumer N, Larbig W, Taub E (1995). Phantom-limb pain as a perceptual correlate of cortical organization following arm amputation. Nature 375: 482-484.
Foster R H, Markham A (2000). Levobupivacaine: a review of its pharmacology and use as a local anaesthetic. Drugs 59: 551-579.
Hari R, Karhu J, Hamalainen M, Knuutila J, Salonen O, Sams M, Vilkman V (1993). Functional organization of the human first and second somatosensory cortices: a neuromagnetic study. Eur J Neurosci 5: 724-734.
Johansson R S, Birznieks I (2004). First spikes in ensembles of human tactile afferents code complex spatial fingertip events. Nat Neurosci 7: 170-177.
Johansson R S, Vallbo A B (1979). Detection of tactile stimuli. Thresholds of afferent units related to psychophysical thresholds in the human hand. J Physiol 297: 405-422.
Kaas J H (1997). Topographic maps are fundamental to sensory processing. Brain Res 44: 107-112.
Katz D (1989). The world of touch. Lawrence Erlbaum Associates, London.
Klatsky R L, Lederman S, Reed C (1987). There's more to touch than meets the eye: The salience of object attributes for haptics with and without vision. J Exp Psych General 116: 356-369.
Maldjian J A, Gottschalk A, Patel R S, Detre J A, Alsop D C (1999). The sensory somatotopic map of the human hand demonstrated at 4 Tesla. Neuroimage 10: 55-62.
Merzenich M M, Jenkins W M (1993). Reorganization of cortical representations of the hand following alterations of skin inputs induced by nerve injury, skin island transfers, and experience. J Hand Ther 6: 89-104.
Merzenich M M, Kaas J H, Sur M, Lin C S (1978). Double representation of the body surface within cytoarchitectonic areas 3b and 1 in "S1" in the owl monkey (*Aotus trivirgatus*). J Comp Neurol 181: 41-74.
Merzenich M M, Kaas J H, Wall R J, Nelson M, Sur D, Felleman D (1983). Topographic reorganization of somatosensory cortical areas 3B and 1 in adult monkeys following restricted desfferentiation. Neuroscience 8: 33-55.
Merzenich M M, Nelson R J, Kaas JHea (1987). Variability in hand surface representations in areas 3 b and 1 in adult own and squirrel monkeys. J Comp Neurol 258: 281-297.
Merzenich M M, Nelson R J, Stryker M S, Cynader M S, Schoppman A, Zook J M (1984). Somatosensory cortical map changes following digit amputation in adult monkeys. J Comp Neurol 224: 591-605.
Ramachandran V (1998). Consciousness and body image: lesson from phantom limbs, Capgras syndrome and pain asymbolia. Philosophical Transactions of the Royal Society of London B; Biological Sciences 353: 1851-1859.
Ramachandran V S, Stewart M, Rogers-Ramachandran DC (1992). Perceptual correlates of massive cortical reorganization. Neuroreport 3: 583-586.
Rosen B, Bjorkman A, Lundborg G (2006). Improved sensory relearning after nerve repair induced by selective temporary anaesthesia—a new concept in hand rehabilitation. J Hand Surg [Br] 31: 126-132.
Rossini P M, Martino G, Narici L, Pasquarelli A, Peresson M, Pizzela V, Tecchio F, Torrioli G, Romani G L (1994). Short-term brain plasticity in humans: transient finger representation changes in sensory cortex somatotopy following ischemic anesthesia. Brain Res 642: 169-177.
van Westen D, Fransson P, Olsrud J, Rosen B, Lundborg G, Larsson E-M (2004). Finger somatotopy in area 3B: a fMRI study. BMC Neurosci 5: 28.

The invention claimed is:

1. A method for improving sensibility of an anatomical body part of a patient suffering from neuropathy, comprising the steps:
applying a local anesthetic substance on a neighboring body part adjacent to the anatomical body part suffering from neuropathy,
wherein the neighboring body part is a crus or forearm of a patient adjacent to the anatomical boy part suffering from neuropathy, and
wherein the anatomical body part suffering from neuropathy is a foot or hand, respectively, of the patient thereby improving the sensibility of said foot or hand.

2. The method according to claim 1, wherein said neuropathy is associated with exposure to vibrations.

3. The method according to claim 1, wherein said neuropathy is associated with diabetes.

4. The method according to claim 1, wherein said neuropathy is associated with nerve compression lesions.

5. The method according to claim 4, wherein said nerve compression lesions are associated with carpal tunnel syndrome.

6. The method according to claim 1, wherein the local anesthetic substance is selected from the group consisting of lidocaine, prilocalne, bupivacain, levobupivacain, rupivacain, and elyzol.

7. The method according to claim 1, further comprising the step of applying a protective cover over the foot or hand of the patient which is not to be anaesthetized in order to inhibit anesthesia of the foot or hand which is not to be anaesthetized.

8. The method according to claim 1, wherein the anesthetic substance has a long term effect.

9. The method according to claim 1, wherein the anesthetic substance is combined with another medical agent which facilitates penetration of the local anesthetic substance to nerve structures in deeper skin layers.

10. The method according to claim 1, wherein the local anesthetic substance is a cream.

11. The method according to claim 1, wherein the local anesthetic substance is applied by use of a device in the form of a cover having a suitable size and shape to fit the anatomical shape of the neighboring body part.

12. The method according to claim 11, wherein the cover is selected from the group consisting of plaster, stocking, patch, sleeve, and socket.

13. The method according to claim 11, wherein the cover has a suitable size and shape to be applied to an anterior aspect of the neighboring body part.

14. The method according to claim 11, wherein the cover has a suitable size and shape to be applied to the neighboring body part selected from the group consisting of a forearm and crus.

15. The method according to claim 1, wherein said applying the local anesthetic substance on the neighboring body part improves the sensory functions of the anatomical body part suffering from neuropathy by expanding the cortical projection of the neighboring body part into the adjacent body part suffering from neuropathy.

* * * * *